United States Patent

Qin et al.

Patent Number: 5,807,249
Date of Patent: Sep. 15, 1998

[54] REDUCED STIFFNESS, BIDIRECTIONALLY DEFLECTING CATHETER ASSEMBLY

[75] Inventors: Jay J. Qin, Santa Clara; Aurelio Valencia, East Palo Alto; Scott H. West, Tracy, all of Calif.

[73] Assignee: Medtronic, Inc., Minneapolis, Minn.

[21] Appl. No.: 791,129

[22] Filed: Feb. 13, 1997

Related U.S. Application Data

[60] Provisional application No. 60/011,807, Feb. 16, 1996.

[51] Int. Cl.⁶ ............................................... A61B 5/04
[52] U.S. Cl. ..................... 600/374; 607/119; 607/122; 606/41
[58] Field of Search ............................. 128/642; 607/116, 607/119, 122; 600/146, 149, 150, 373–375, 377, 378–381, 585; 604/95, 282; 606/41

[56] References Cited

U.S. PATENT DOCUMENTS

| | | |
|---|---|---|
| 2,498,692 | 2/1950 | Mains . |
| 3,557,780 | 1/1971 | Sato . |
| 3,605,725 | 9/1971 | Bentov . |
| 4,718,419 | 1/1988 | Okada . |
| 5,318,525 | 6/1994 | West et al. .............................. 607/122 |
| 5,327,905 | 7/1994 | Avitall ..................................... 607/122 |
| 5,397,304 | 3/1995 | Truckai . |
| 5,465,716 | 11/1995 | Avitall .................................... 128/642 |
| 5,478,330 | 12/1995 | Imran et al. ............................ 607/122 |
| 5,487,757 | 1/1996 | Truckai et al. . |
| 5,662,606 | 9/1997 | Cimino et al. ......................... 128/642 |

*Primary Examiner*—Lee S. Cohen
*Assistant Examiner*—David M. Ruddy
*Attorney, Agent, or Firm*—Townsend and Townsend and Crew LLP

[57] ABSTRACT

A reduced stiffness, bidirectionally deflecting catheter assembly (2) includes a handle (4) and flexible catheter shaft (6) with a tip section (12) secured to its distal end (14). The tip section has a radially offset, longitudinally extending core wire lumen (42) through which a tapered core wire (24), extending from a core wire manipulator (56) on the handle, passes. The core wire manipulator can be moved in two different directions (58, 60) to pull or push on the core wire to cause the tip section to deflect axially in opposite directions in the same plane. The ends of the core wire are non-rotatably secured to the handle and the tip section so that rotating the handle about its axis (63) causes the tip section to deflect laterally due to torsionally forces exerted on the tip section by both the catheter shaft and the core wire. The taper on the core wire determines the size and shape of the curved tip section when the tip is axially deflected.

13 Claims, 4 Drawing Sheets

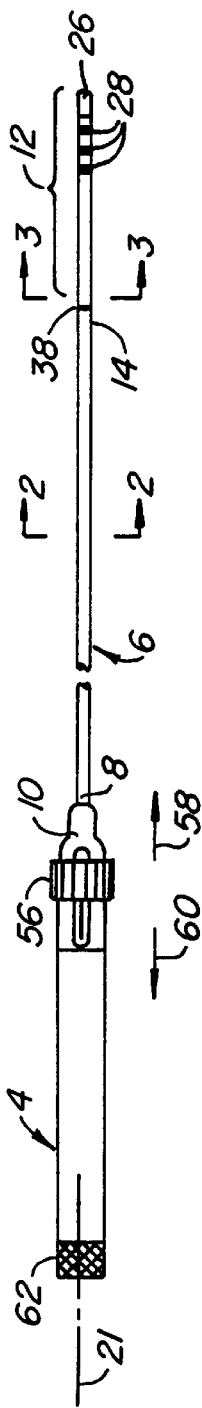
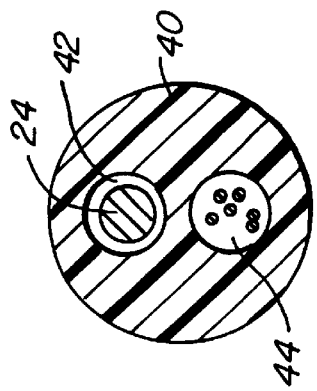
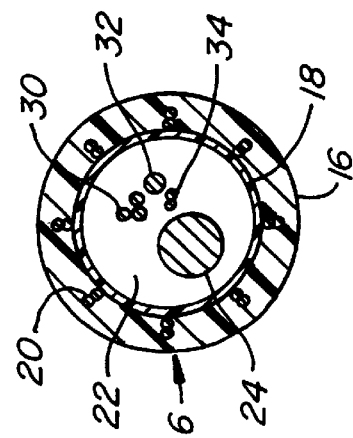
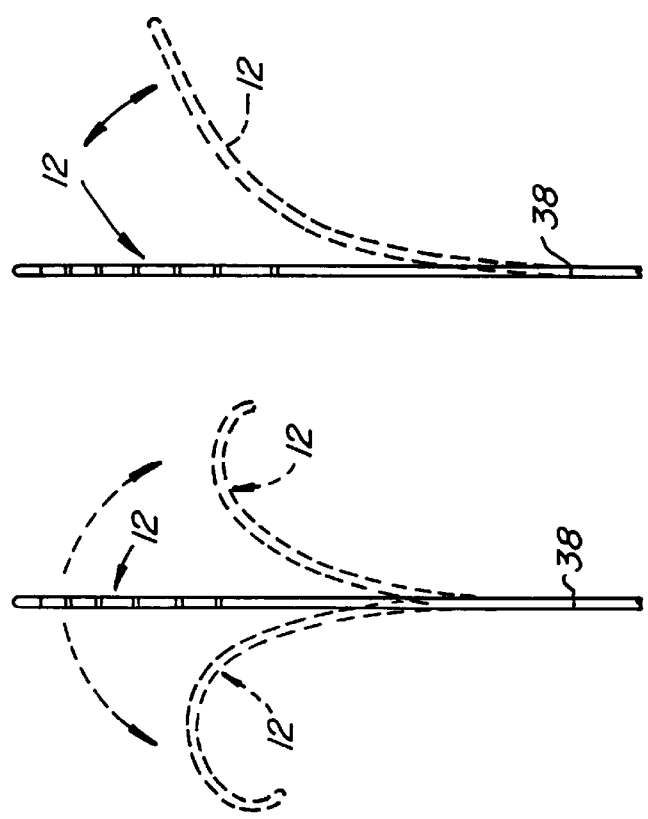
FIG. 1.
FIG. 1A.
FIG. 1B.
FIG. 2.
FIG. 3.

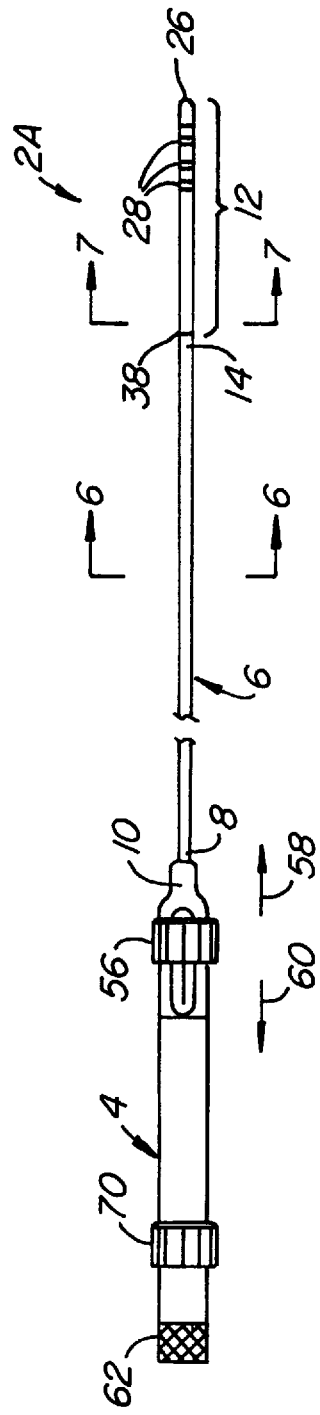
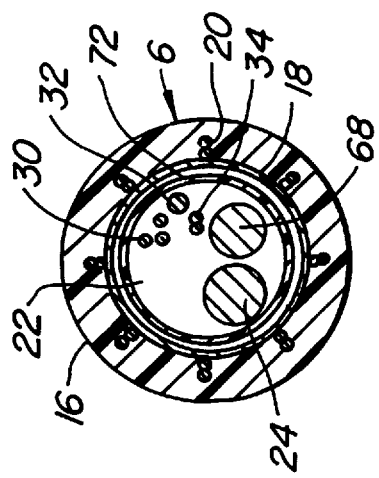
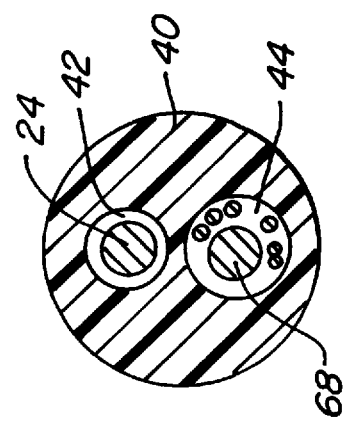
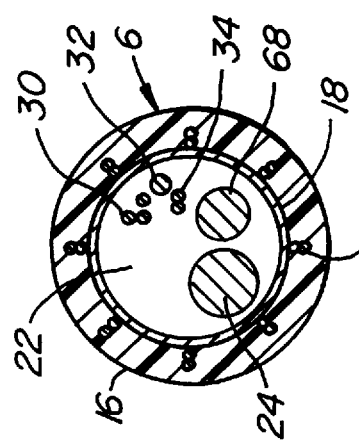

REDUCED STIFFNESS, BIDIRECTIONALLY DEFLECTING CATHETER ASSEMBLY

CROSS-REFERENCE TO RELATED APPLICATION

This application claims the benefit of U.S. provisional application No. 60/011,807, filed Feb. 16, 1996, entitled "REDUCED STIFFNESS, BIDIRECTIONALLY DEFLECTING CATHETER ASSEMBLY, which disclosure is incorporated herein by reference.

BACKGROUND OF THE INVENTION

The design of electrophysiology catheters, used for cardiac mapping and ablation, is always in result of certain compromises and tradeoffs. Such catheters commonly employ a handle to which a flexible hollow catheter shaft extends. A tip section extends from the distal end of the catheter shaft and is typically more flexible than the catheter shaft. One or more electrodes are carried by the tip section to provide the desired mapping, pacing, ablation or catheterization. One common type of electrophysiology catheter permits the tip section to be axially deflected by pulling on a relatively thin, flexible manipulator wire. The distal end of the manipulator wire is typically connected near the tip of the tip section while at the proximal end of the manipulator wire is typically connected to some type of slider carried by the handle. Pulling on the manipulator wire causes the tip of the tip section to deflect axially to the desired shape. (Pulling on the manipulator wire moves the tip both radially and axially to create the curve in the tip. This complex movement is termed axial deflection for ease of reference.) Since the catheter shaft and tip section are typically radiopaque, this movement can be observed by the physician.

In some cases, additional capabilities are desired from an electrophysiology catheter. For example, the catheter shown in U.S. Pat. No. 5,487,757, the disclosure of which is incorporated by reference, shows a catheter in which the tip section can be deflected axially by pulling on a manipulator wire, the size of the curved tip section can be changed by sliding a stiffener wire to different positions along the tip section, and the tip section can be deflected laterally by rotating a core wire extending from a rotatable ring carried by the handle to the tip section. While this catheter assembly provides a great deal of control for the user, in some situations the catheter is not as flexible as is desired.

SUMMARY OF THE INVENTION

The present invention is directed to an electrophysiology catheter assembly which uses a single core wire to achieve one or more of the following: (1) tip deflection in two, opposite directions in the same plane; (2) torque transmission from the handle to the tip section; and (3) control of the size of the axially deflected curve of the tip.

The catheter assembly includes a handle, a hollow, flexible catheter shaft and a tip section secured to the distal end of the catheter shaft. The tip section has a radially offset, longitudinally extending core wire lumen through which a core wire, extending from the handle at its proximal end to the tip section at its distal end, passes. The core wire is secured to a core wire manipulator carried by the handle. The core wire manipulator can be moved, preferably in two different directions, to pull or push on the core wire to cause the tip section to deflect axially in opposite directions in the same plane.

The proximal and distal ends of the core wire are preferably non-rotatably secured to the handle and the tip section so that rotating the handle about its longitudinal axis causes the axially deflected tip section to deflect laterally due to torsional forces exerted on the tip section by both the catheter shaft and the core wire.

The tip section can include a stiffener element, such as a hypotube, along a portion of its length so that, for example, the distal end of the tip section remains essentially straight when the remainder of the tip section is curved in its axially deflected condition. This can be very useful for certain electrophysiology procedures.

A spring coil can be used along at least a portion of, and preferably the entire length of, the proximal shaft to increase the columnar strength. This substantially increased columnar strength reduces undulation and waviness in the catheter shaft while allowing the catheter shaft to remain flexible.

Another feature of the invention is the use of a taper on the same core wire to determine the size and shape of the axially deflected tip. The physician may be provided with a selection of, for example, four different electrophysiology catheter assemblies depending on the particular size and shape desired for the tip section when axially deflected. Also, the tip section can be provided with different size curves by using a longitudinally sliding stiffener wire which can be extended by the user different distances into the tip section. The further the stiffener wire extends into the tip section, the tighter the radius of curvature the tip section typically assumes when deflected axially. This provides a simpler, more flexible multicurve design than is present with the catheter disclosed in U.S. Pat. No. 5,487,757.

A range of material stiffness can be provided in the tip section and shaft to optimize performance for different anatomical sites. For example, a stiff tip and shaft plus large curve can be used for mapping and ablation of the right atrial free wall, a soft tip and shaft plus smaller curve can be used for traversing the aortic arch and positioning the tip at the septal portion of the mitral valve annulus.

Other features and advantages of the invention will appear from the following description in which the preferred embodiments have been set forth in detail in conjunction with the accompanying drawings.

BRIEF DESCRIPTION OF THE DRAWINGS

Fig. 1 is a simplified overall view of an electrophysiology catheter assembly made according to the invention;

Fig. 1A is a simplified view of the tip section of FIG. 1 illustrating, in dashed lines, the curvatures of the tip section after having pulled and pushed the core wire of FIGS. 2–4 by pulling and pushing of the core wire slider of FIG. 1;

FIG. 1B is a view of the tip section of the catheter assembly of Fig. 1 illustrating, in dashed lines, a axially deflected tip portion with the distal end of the tip portion being substantially straight due to the use of the hypotube in FIG. 4;

Figs. 2 and 3 are cross-sectional views taken along lines 2—2 and 3—3 of FIG. 1;

FIG. 5 a view similar to that of FIG. 1, of an alternative embodiment of an electrophysiology catheter assembly including a slidable stiffener wire;

FIGS. 6 and 7 are cross-sectional views taken along lines 6—6 and 7—7 of FIG. 5;

Fig. 8 is a cross-sectional view similar to FIG. 6, but of a catheter assembly including a spring coil along the catheter shaft.

DESCRIPTION OF THE PREFERRED EMBODIMENTS

Figure 4:
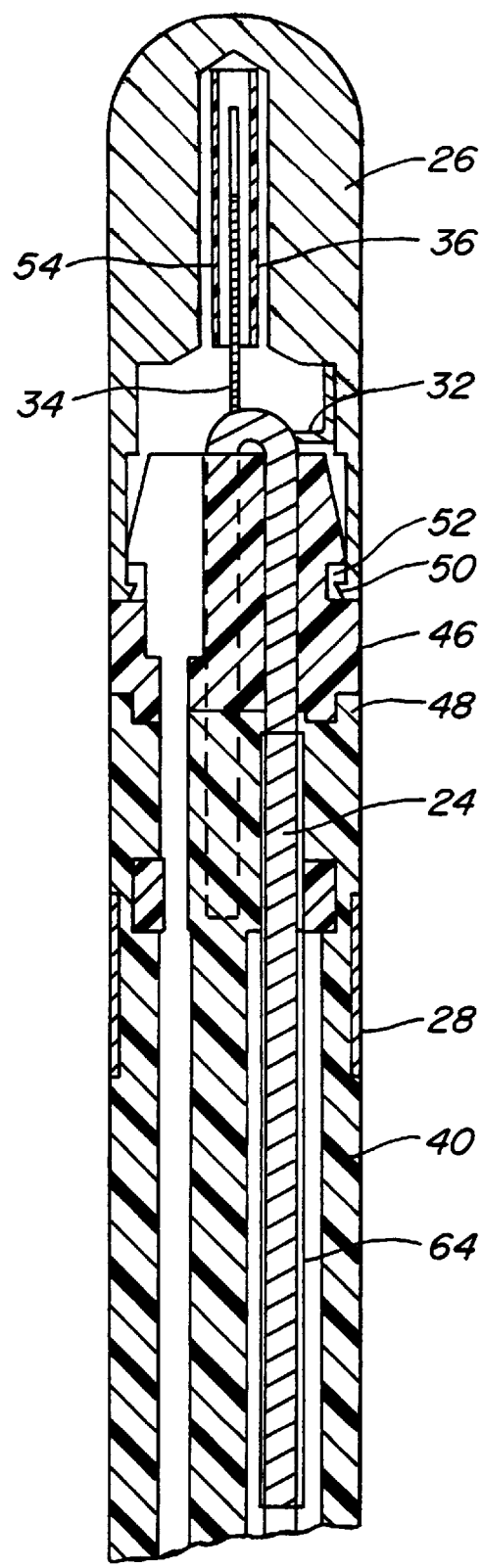
FIG. 4 is an enlarged cross-sectional view of the tip of the tip section of the catheter assembly of FIG. 1.

FIG. 1 illustrates an electrophysiology catheter assembly 2 including a handle 4 from which a catheter shaft 6 extends. Catheter shaft 6 has a proximal end 8 extending from a end cap 10 of handle 4. Catheter assembly 2 also includes a tip section 12 extending from the distal end 14 of catheter shaft 6. Handle 4 is preferably a simplified version of one of the handles shown in U.S. patent application No. 08/343,310, the disclosure of which is incorporated by reference.

FIG. 2 shows that catheter shaft 6 includes a jacket 16 surrounding a polyetherimide tubing 18. Jacket 16 is made of Pebax®, a polyamide polyether block copolymer of Elf Atochem, Inc. of Philadelphia, Pa. Stainless steel braiding wire 20 is embedded within jacket 16. The construction of catheter shaft 6 provides catheter assembly 2 with reasonable torque transmitting ability. Preferably the combination of catheter shaft 6 and tip section 12 has a torsional stiffness of about 0.50 to 1.5 inch-ounce per 120 cm, and more preferably about 0.80 inch-ounce per 120 cm, when the proximal end of the catheter shaft is rotated about 3 turns about the longitudinal axis 21 of handle 4.

Catheter shaft 6 defines a hollow interior 22 through which a stainless steel core wire 24 passes. In addition, various electrical wires pass through hollow interior 22, the number and composition depending upon the use to which catheter assembly is to be put. In the disclosed embodiment, tip section 12 includes a higher power, ablation capable tip electrode 26 and three lower power, mapping electrodes 28. These various electrodes are connected to insulated mapping electrode wires 30 and an ablation electrode wire 32. RF ablation energy is typically conducted through wire 32 to electrode 26. (Wires 30, 32 can be of different sizes or identical.) A pair of thermocouple wires 34 also pass through hollow interior 22 and terminate within a cavity 36 formed in tip electrode 26 as shown in FIG. 4. Tip section 12 is secured to distal end 14 of catheter shaft 6 at a junction 38 typically by RF energy or hot air thermo-welding techniques.

Tip section 12 includes a tip tubing body 40 made of Pebax®. Body 40 has a pair of longitudinally extending lumens 42, 44. Core wire 24 passes through lumen 42 while the remainder of the wires pass through lumen 44. The doubled-over end of core wire 24 passes into and is secured to insulator 46, see FIG. 4. Lumen 42 is radially offset so that pulling or pushing core wire 24 exerts a radially offset force on tip section 12.

Insulator 46, typically made of PEEK (poly-ether-ether-keytone), is thermally or adhesively bonded to the distal end 48 of body 40. Tip electrode 26, typically made of platinum, is secured in place through the engagement of an inwardly extending lip 50 fitting within a annular groove 52 formed in insulator 46. As can be seen in FIG. 4, ablation electrode wire 32 is welded, brazed, or otherwise secured to tip electrode 26, as is conventional. A polyimide tubing 54 is used to surround and electrically insulate thermocouple wires 34 from tip electrode 26.

The proximal end, not shown, of core wire 24 is secured to a core wire slider 56 carried by handle 4. With tip section 12 in the straight condition as shown in FIG. 1, slider 12 can be moved in a distal direction 58, pushing on core wire 24, or a proximal direction 60, pulling on core wire 24. Doing so causes tip section 12 to deflect axially in two different directions in the same plane; this is illustrated in FIG. 1A. Unlike conventional manipulator wires, core wire 24 has sufficient columnar strength so as not to buckle when slider 12 is moved in distal direction 58. Thus, catheter assembly 2 provides the user with a bidirectional deflectable catheter assembly using slider 56 by moving slider 56 in either distal direction 58 or proximal direction 60. Handle 4 also includes an electrical connector 62 to which wires 30, 32, 34 are connected.

Core wire 24 is also used to cause axially deflected tip section 12 to deflect laterally. Lateral deflection occurs when handle 4 is rotated about its longitudinal axis 21. Core wire 24 has a torsional stiffness of about 0.1–0.5 inch-ounce per 120 cm, and preferably about 0.20 inch-ounce per 120 cm, when the proximal end of the core wire is rotated about 3 turns about longitudinal axis 21. The combination of tip section 12 and catheter shaft 6 has a torsional stiffness of about 0.50 to 2.0 inch-ounce, and preferably at least about 0.80 inch-ounce, per 120 cm of length, when handle 4 is rotated about 3 turns around axis 21. Therefore, torsional stiffness for lateral deflection of tip 12 is provided in substantial part by both catheter shaft 6 and core wire 24.

In some cases it is desired that the most distal portion of tip section 12 remain substantially straight when tip section 12 is deflected axially. To accommodate this, a stiffener element, such as a hypotube 64 shown in FIG. 4, can be used. Hypotube 64 is positioned within a distal section of lumen 42 and, in the preferred embodiment is about 8 to 15 mm long. The difference between deflecting tip section 12 with and without hypotube can be seen by comparing FIG. 1A (without hypotube 64) and FIG. 1B (with hypotube 64). As can be seen, the distal-most end of tip section 12 is relatively straight compared with the corresponding distal-most section of tip section 12 of FIG. 1A. It has been found that this shape is desirable in some circumstances.

FIGS. 5–7 illustrate an alternative embodiment of the invention with like reference numerals referring to like elements. The primary difference between catheter assembly 2A of FIGS. 5–7 and catheter assembly 2 of FIGS. 1–4 is the addition of a stiffener wire 68 which extends from a stiffener wire slider 70 carried by handle 4 into various positions along tip section 12 depending on the particular location of slider 70. Advancing slider 70 in the direction of arrow 58 extends stiffener wire 68 further into tip section 12; thus tip section 12, when axially deflected by the manipulation of slider 56, should have a smaller radius of curvature because of the additional stiffness imparted to tip section 12, especially along the proximal portion of the tip section.

FIG. 8 illustrates a cross-sectional view similar to that of FIG. 6 of a further alternative embodiment of the invention. In this embodiment a spring coil 66 extends along the entire length of catheter shaft 6. Spring coil 72 is preferably made of tightly wound 0.007 inch (0.18 mm) diameter stainless steel. Spring coil 77 is anchored at each end to catheter shaft 6 so that a slight compression is built into the spring coil. Use of spring coil 72 increases the columnar strength of catheter shaft 6 to prevent waviness of the catheter shaft during use and to reduce catheter shaft undulation when tip section 12 is deflected.

One of the key features of the invention is to provide a family of catheters which, as a group, offer all the performance characteristics which are needed for ablation. Depending on the particular location in the heart, different catheter sizes and performance characteristics are required for effective and easy ablation of supraventricular tachycardia (SVT). For example, when performing a catheter ablation on the right atrial free wall above the tricuspid annulus, a large curve, relatively stiff shaft, and relatively stiff tip are commonly required for the best results. The large curve is required so that the catheter tip will span the large distance from the inferior vena cava (entry point for the catheter) to the right atrial free wall. The stiff shaft and stiff tip are required to provide good stability of the tip against the beating free wall, and to permit maximum tip-to-tissue pressure to be generated. The high blood flow rates in this area of the heart make it essential that the tip contact be excellent to insure efficient delivery of RF energy to the tissue.

On the other hand, when performing a catheter ablation on the septal side of the mitral valve annulus, a small curve, relatively soft tip and relatively soft shaft are often optimal. The soft shaft allows the catheter to negotiate the 180° C. bend of the aortic arch. The soft tip allows the device to pass though the aortic valve without causing damage. The small curve allows access to septal sites which are very close to the catheter shaft when the tip is deflected to approximately 180° C.

Between these two extreme cases, a catheter with a "medium" curve size and an intermediate value for tip and shaft stiffness is useful for many other locations around the tricuspid annulus on the right side of the heart, and similar intermediate qualities of stiffness and size are usually appropriate for left lateral (and some septal) sites on the mitral valve annulus. In addition to ablation on or near the valves for SVT, different shaft and tip stiffness characteristics are required at various locations elsewhere in the heart, when performing ablation for atrial tachycardias (AV) (AV nodal reentrant tachycardia, AV junction ablation, atrial flutter, atrial fibrillation) and ventricular tachycardias.

Figure 9:
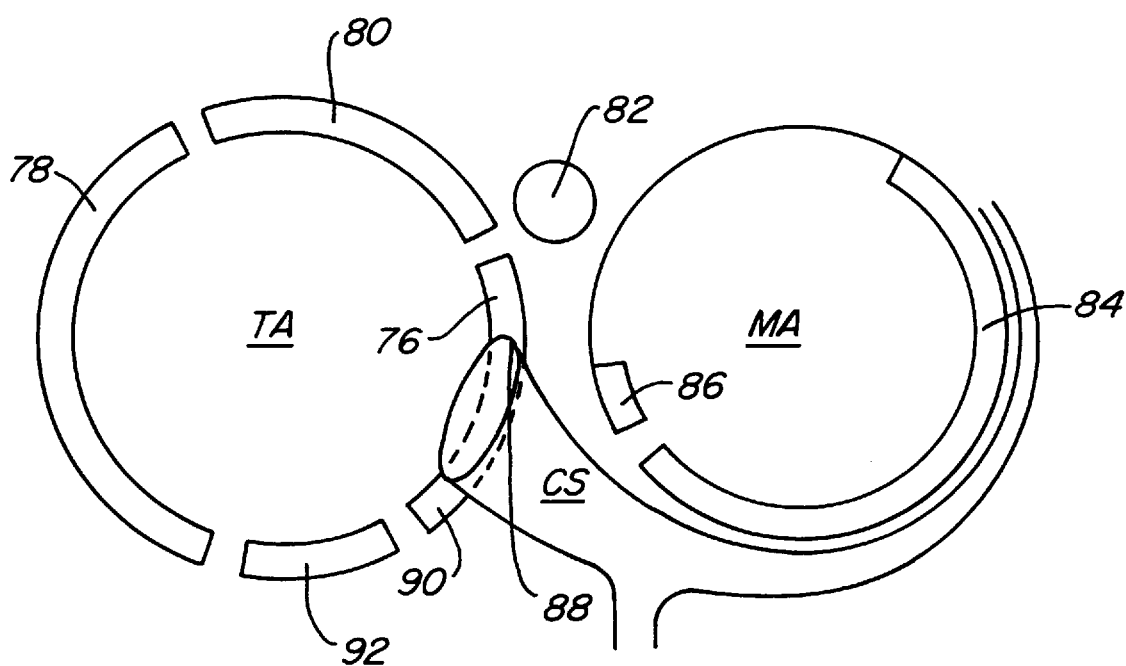
FIG. 9 is a schematic illustration of various anatomical sites within the heart and the different shaft stiffness, tip stiffness and size of curved tip appropriate for the different sites.

Previous catheter designs have typically offered a range of curve sizes for different anatomical sites. The present invention represents a new concept in which the three most important catheter performance characteristics (curve size, tip stiffness, shaft stiffness) are optimized according to anatomical site. FIG. 9 is a simplified view of a portion of a heart including the tricispid annulus TA, mitral annulus MA and coronary sinus CS. The following summarizes the performance characteristics most commonly required at a variety of locations indicated in FIG. 9. The term "reach" refers to the radial distance the tip of the tip section moves from the central axis when deflected 90° C.; a "short reach", such as 35 mm, refers to a smaller radius while a "long reach", such as 65 mm, refers to a longer radius. "R" and "L" stand for right and left.

| | | CHARACTERISTICS | | |
|---|---|---|---|---|
| REF. NO. | LOCATION | SHAFT | TIP | REACH |
| 76 | AV Nodal Re-entry | Medium | Med. to Stiff | Med. to Long |
| 78 | R. Lateral (free wall) | Med. to Stiff | Stiff | Med. to Long |
| 80 | R. Anterior Anteroseptal | Medium | Medium | Med. to Long |
| 82 | Bundle of HIS | Medium | Medium | Medium |
| 84 | L. Lateral (free wall) Accessory Pathway | Soft | Medium | Short to Med. |
| 86 | L. Posteroseptal | Soft | Soft | Short |
| 88 | R. Midseptal | Medium | Medium | Med. to Long |
| 90 | R. Posteroseptal | Medium | Medium | Med. to Long |

-continued

| | | CHARACTERISTICS | | |
|---|---|---|---|---|
| REF. NO. | LOCATION | SHAFT | TIP | REACH |
| 92 | R. Posterior Accessory | Medium | Medium | Med. to Long |

Shaft bending stiffness preferably ranges from 0.052 lb to 0.170 lb, and more preferably 0.063 lb to 0.161 lb. The bending stiffness of the tip section preferably ranges from 0.032 lb to 0.117 lb, and more preferably from 0.066 lb to 0.088 lb. The terms soft, medium and stiff refer to values at the lower range (typically lower ⅓), middle range (typically middle ⅓), and upper range (typically upper ⅓) of these values. These stiffness values are for forces measured as follows.

For shaft stiffness, immerse the catheter shaft into a 37° C. water bath. Clamp the catheter near the center of the shaft. Place a universal force gauge in contact with the shaft, approximately 4 cm from the clamp. Zero the gauge. Lower the gauge 15 mm to deflect the shaft. Record the maximum force as the shaft bending stiffness value.

For tip section stiffness, a compression tester is used above a block covered with 600 grit sandpaper. The catheter shaft is gripped by the tester at the shaft's distal end. The tip of the tip section is placed against the sandpaper at an angle of between about 100°–200° C. from a perpendicular to the sandpaper. The compression tester is moved towards the sandpaper a distance of one inch, or until the tip of the tip section slips, whichever first occurs. The maximum axial force exerted on the tip section by the compression tester is recorded as the tip section bending stiffness value.

These tests were conducted in accordance with Good Laboratory Procedures (GLP) regulations.

In use, the user first selects a catheter assembly 2 or 2A. If a catheter assembly 2 is selected, a catheter assembly having a core wire 24 with a particular taper (or other cross-sectional profile) along tip section 12 to produce the desired shape when axially deflected is selected for the particular procedure. A particular combination of tip and shaft stiffness is also selected, appropriate for the anatomical site. If a catheter assembly 2A is selected, the shape of the axially deflected tip section 12 can be adjusted during use utilizing stiffener wire slider 70 to move stiffener wire 68 axially through lumen 44. In either case, tip section 12 is axially deflected in one of two opposite directions lying in the same plane as suggested in FIG. 1A by either pushing on slider 56 or pulling on slider 56. Lateral deflection of the axially-deflected tip section 12 is achieved by rotating handle 4 about its longitudinal axis 4. The torquing force which causes the lateral deflection of tip section 12 is transmitted to the tip section in substantial part by both catheter shaft 6 and core wire 24. With the embodiment of FIGS. 5–7, the shape of axially deflected catheter tip 12 can be changed during use by moving stiffener wire 68.

Modification and variation can be made to the disclosed embodiments without departing from the subject of the invention as defined in the following claims.

What is claimed is:

1. An electrophysiology catheter assembly comprising:
  a handle having a longitudinal axis, said handle comprising a core wire manipulator;
  a hollow flexible catheter shaft having a proximal end and a distal end, the proximal end of the catheter shaft secured to the handle;

a tip section secured to the distal end of the catheter shaft, said tip section comprising at least one electrode;

said tip section comprising a radially offset, longitudinally extending core wire lumen;

a core wire having an axis extending longitudinally therethrough and having a proximal end coupled to the core wire manipulator and a distal end passing through the core wire lumen;

said distal end of the core wire secured to the tip section; and said core wire manipulator movable in first and second axial directions so to place said core wire in tension and compression thereby deflecting said tip section in first and second opposite radial directions in the same plane and into first and second curved shapes disposed on opposite sides of said core wire axis, wherein said core wire has a strength sufficient to resist buckling when compressed axially.

2. The catheter assembly according to claim 1 wherein:

said core wire is nonrotatably coupled to the handle so that rotating the handle about said longitudinal axis causes said axially deflected tip section to deflect laterally due to torsional forces exerted on the tip section by both said catheter shaft and the core wire;

a combination of said tip section and catheter shaft having a torsional stiffness of about 0.50 to 2.0 inch-ounce per 120 cm of length when the proximal end of said catheter shaft is rotated about 3 turns;

said core wire having a torsional stiffness of at least about 0.1 to 0.5 inch-ounce per 120 cm of length when said proximal end of said core wire is rotated about 3 turns.

3. The catheter assembly according to claim 1 wherein said tip section comprises a stiffener element extending along a portion of the length of the tip section for holding a distal end of the tip section generally straight when a remainder of the tip section is curved.

4. The catheter assembly according to claim 3 wherein:

said tip section comprises a tip electrode;

said distal end of the core wire is secured to the tip section at a position adjacent to said tip electrode; and said stiffener element is adjacent to and proximal of said position.

5. The catheter assembly according to claim 1 wherein said catheter shaft further comprises a spring coil element along said catheter shaft.

6. The catheter assembly according to claim 5 wherein said spring coil element has turns adjacent to one another.

7. The catheter assembly according to claim 1 further comprising a longitudinally slidable stiffener wire having a proximal end connected to a stiffener wire manipulator carried by the handle and a distal end freely longitudinally movable within said tip section.

8. The catheter assembly according to claim 1 wherein the core wire is a variable stiffness core wire.

9. The catheter assembly according to claim 8 wherein said core wire is a tapered core wire.

10. The catheter assembly according to claim 1 wherein said catheter shaft has a bending stiffness of between about 0.052 lb and 0.170 lb and said tip section has a bending stiffness of between about 0.032 lb and 0.117 lb, with said catheter shaft being stiffer than said tip section.

11. An electrophysiology catheter assembly comprising:

a handle having a longitudinal axis, said handle comprising a core wire manipulator;

a hollow flexible catheter shaft having a proximal end and a distal end, the proximal end of the catheter shaft secured to the handle;

a tip section secured to the distal end of the catheter shaft, said tip section comprising at least one electrode;

said tip section comprising a radially offset, longitudinally extending core wire lumen;

a core wire having an axis extending longitudinally therethrough and having a proximal end coupled to the core wire manipulator and a distal end passing through the core wire lumen;

said distal end of the core wire secured to the tip section;

said core wire manipulator movable in first and second axial directions so to place said core wire in tension and compression thereby deflecting said tip section in first and second opposite radial directions in the same plane and into first and second curved shapes disposed on opposite sides of said core wire axis, said core wire being nonrotatably coupled to the handle so that rotating the handle about said longitudinal axis causes said axially deflected tip section to deflect laterally due to torsional forces exerted on the tip section by both said catheter shaft and the core wire;

a combination of said tip section and said catheter shaft having a torsional stiffness of at least about 0.80 inch-ounce per 120 cm of length when said proximal end of said catheter shaft is rotated about 3 turns; and said core wire having a torsional stiffness of at least about 0.20 inch-ounce per 120 cm of length when said proximal end of said core wire is rotated about 3 turns.

12. The assembly according to claim 11, wherein said catheter shaft comprises a spring coil along at least a substantial portion of the catheter shaft, said spring coil having turns adjacent to one another.

13. The assembly according to claim 11 further comprising a longitudinally slidable stiffener wire having a proximal end connected to a stiffener wire manipulator carried by the handle and a distal end freely longitudinally movable within said tip section.

* * * * *